US009239298B2

(12) United States Patent
Nagai et al.

(10) Patent No.: US 9,239,298 B2
(45) Date of Patent: Jan. 19, 2016

(54) OPTICAL MEASUREMENT PROBE, AND OPTICAL MEASUREMENT DEVICE PROVIDED WITH THE SAME

(71) Applicants: SHIMADZU CORPORATION, Kyoto-shi, Kyoto (JP); HONDA MOTOR CO., LTD., Tokyo (JP)

(72) Inventors: Tetsuya Nagai, Nishinomiya (JP); Nobuyuki Iwai, Kyoto (JP); Yasuyuki Furukawa, Kyoto (JP); Ryoji Hiraoka, Hirakata (JP); Isao Azumagakito, Wako (JP); Satoru Okada, Wako (JP)

(73) Assignees: SHIMADZU CORPORATION, Kyoto-shi (JP); HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 14/481,230

(22) Filed: Sep. 9, 2014

(65) Prior Publication Data
US 2015/0085283 A1 Mar. 26, 2015

(30) Foreign Application Priority Data

Sep. 20, 2013 (JP) ................. 2013-195553

(51) Int. Cl.

| G01J 3/28   | (2006.01) |
| G01N 21/958 | (2006.01) |
| G01M 15/04  | (2006.01) |
| G01N 21/94  | (2006.01) |
| G02B 1/02   | (2006.01) |
| G01J 5/08   | (2006.01) |

(Continued)

(52) U.S. Cl.
CPC .............. *G01N 21/958* (2013.01); *F02P 13/00* (2013.01); *G01D 5/353* (2013.01); *G01J 5/0014* (2013.01); *G01J 5/042* (2013.01); *G01J 5/043* (2013.01); *G01J 5/0821* (2013.01); *G01M 15/042* (2013.01); *G01N 21/15* (2013.01); *G01N 21/67* (2013.01); *G01N 21/94* (2013.01); *G02B 1/02* (2013.01); *F02D 35/022* (2013.01); *G01J 3/0218* (2013.01); *G01N 2201/08* (2013.01); *G02B 6/262* (2013.01); *H01T 13/40* (2013.01)

(58) Field of Classification Search
CPC ............... G01J 3/02; G01J 3/10; G01J 3/28; G01J 3/2803; G01J 3/2823
USPC ...................................... 356/300–334; 385/38
See application file for complete search history.

(56) References Cited

U.S. PATENT DOCUMENTS

| 6,879,741 B2 *    | 4/2005 | Salerno et al. .................. 385/12 |
| 2003/0053050 A1 * | 3/2003 | Potyrailo et al. .............. 356/326 |

(Continued)

FOREIGN PATENT DOCUMENTS

| JP | 20141-241753 A | 12/2011 |
| JP | 2012-118080 A  | 6/2012  |

*Primary Examiner* — Abdullah Nur
(74) *Attorney, Agent, or Firm* — Westerman, Hattori, Daniels & Adrian, LLP

(57) ABSTRACT

There are provided an optical measurement probe capable of obtaining a more stable measurement result, and an optical measurement device provided with the same. An incidence surface of an optical window to be used in a high temperature environment is covered by a deposited film. The optical window is formed of sapphire, and the deposited film is formed from $SiO_2$. Adhesion of dirt to the incidence surface, and an influence, on a measurement result, of the adhesion of dirt on the incidence surface can thereby be prevented, and a more stable measurement result can be obtained.

13 Claims, 5 Drawing Sheets

(51) Int. Cl.
*G01J 5/00* (2006.01)
*G01J 5/04* (2006.01)
*F02P 13/00* (2006.01)
*G01N 21/15* (2006.01)
*G01N 21/67* (2006.01)
*G01D 5/353* (2006.01)
*G01J 3/02* (2006.01)
*G02B 6/26* (2006.01)
*F02D 35/02* (2006.01)
*H01T 13/40* (2006.01)

(56) References Cited

U.S. PATENT DOCUMENTS

2008/0218738 A1\* 9/2008 Trainer .......................... 356/72
2012/0143458 A1 6/2012 Winklhofer et al.

\* cited by examiner

OPTICAL MEASUREMENT PROBE, AND OPTICAL MEASUREMENT DEVICE PROVIDED WITH THE SAME

BACKGROUND OF THE INVENTION

1. Field of the Invention

The present invention relates to an optical measurement probe for guiding light generated in a high temperature environment to an appliance, and an optical measurement device provided with the same.

2. Description of the Related Art

For example, at the time of evaluating the combustion state in a combustion chamber of an internal combustion engine of a car, measurement is performed using an optical measurement probe for guiding light generated at the time of combustion to an appliance (for example, see JP-A-2012-118080, and JP-A-2011-241753). Such an optical measurement probe to be used in a high temperature environment has to be designed by giving enough consideration to heat resistance.

The optical measurement probe is provided with an optical window, and a light guide, for example. Light generated in a high temperature environment enters from an incidence surface of a transparent optical window, and light transmitted through the optical window is guided to an appliance by a light guide formed of an optical fiber, for example. Heat resistance of the optical window is particularly important in the case of such a structure.

SUMMARY OF THE INVENTION

As the material for an optical window as described above, sapphire having high heat resistance and capable of passing light of a wide wavelength range can be used. However, sapphire has a high lipophilic property, and there is a problem that greasy dirt easily adheres to the sapphire.

For example, in a case where the optical window looks into a combustion chamber of an internal combustion engine of a car, soot, engine oil and the like floating in the combustion chamber at the time of combustion come into contact with the incidence surface of the optical window. Thus, when the optical window is formed using sapphire with a high lipophilic property, greasy dirt including soot, engine oil and the like tends to adhere to the incidence surface of the optical window.

When measurement is performed with dirt adhered to the incidence surface of the optical window, the adhered matter may considerably absorb light of a specific wavelength. Also, the amount of received light may be reduced due to the adhered matter preventing transmission of light regardless of the wavelength of light. In this case, even if light emission at the time of combustion is constant, measurement results may vary, and the accuracy of analysis may be reduced.

The present invention has been made in consideration of the above circumstances, and has its object to provide an optical measurement probe capable of obtaining more stable measurement results, and an optical measurement device provided with the same.

An optical measurement probe according to the present invention is for guiding light generated in a high temperature environment to an appliance. The optical measurement probe comprises an optical window and a light guide. The optical window is for transmitting light incident on an incidence surface. The light guide is for guiding light which has passed through the optical window to the appliance. The incident surface of the optical window is covered by a deposited film.

According to such a structure, by covering the incidence surface of the optical window to be used in a high temperature environment by the deposited film, adhesion of dirt to the incidence surface can be prevented. That is, in a case where the optical window is formed of a highly heat-resistant material, dirt may easily adhere to the incidence surface depending on the material, but also in such a case, by covering the incidence surface by the deposited film, adhesion of dirt to the incidence surface can be prevented. Thus, a measurement result can be prevented from being affected by adhesion of dirt to the incidence surface, and a more stable measurement result can be obtained.

The optical window may be formed of sapphire.

According to such a structure, by covering the incidence surface of the optical window formed of sapphire by the deposited film, adhesion of dirt to the incidence surface can be prevented. The optical window that is formed of sapphire is highly heat-resistant and is capable of transmitting light of a wide wavelength range, and is thus suitable for use in a high temperature environment, but on the other hand, it is highly lipophilic, and greasy dirt easily adheres thereto. Thus, with respect to the optical measurement probe to be used in an environment where the temperature is high and adhesion of greasy dirt easily occurs, adhesion of greasy dirt to the incidence surface of the optical window formed of sapphire can be prevented by covering the incidence surface by the deposited film. Thus, a more stable measurement result can be obtained even in an environment where the temperature is high and adhesion of greasy dirt easily occurs.

The deposited film may be formed from $SiO_2$.

According to such a structure, by covering the incidence surface of the optical window by the deposited film formed from $SiO_2$, adhesion of dirt to the incidence surface can be prevented. The deposited film formed from $SiO_2$ is capable of transmitting light of a wide wavelength range, and dirt is not easily adhered thereto. Thus, with respect to the optical measurement probe that is used in an environment where adhesion of greasy dirt easily occurs, by covering the incidence surface of the optical window by the deposited film formed from $SiO_2$, adhesion of greasy dirt to the incidence surface can be prevented, and also, the deposited film can be prevented from causing reduction in the optical property. Accordingly, a more stable measurement result can be obtained even in an environment where adhesion of greasy dirt easily occurs.

Particularly, according to a structure where the incidence surface of the optical window formed of sapphire is covered by the deposited film formed from $SiO_2$, the optical measurement probe which is very suitable for use in an environment where the temperature is high and adhesion of greasy dirt easily occurs, like the inside of the combustion chamber of an internal combustion engine, can be provided.

The deposited film may be formed directly on the incidence surface.

According to such a structure, adhesion of dirt to the incidence surface of the optical window can be prevented by a simple structure of forming the deposited film directly on the incidence surface. Accordingly, a measurement result can be effectively prevented from being affected by adhesion of dirt to the incidence surface by an inexpensive structure, and a more stable measurement result can be obtained.

At least one layer of another film may be interposed between the deposited film and the incidence surface.

According to such a structure, by interposing the other film between the deposited film and the incidence surface, an optical property specific to the film can be provided. Thereby, adhesion of dirt to the incidence surface can be prevented, and the optical measurement probe provided with an optical property suitable for the use environment can be provided.

The other film may be a film having a property of preventing reflection of light, or a property of transmitting only the light of a specific wavelength. Also, the other film may be formed by deposition. That is, a multilayer film having the deposited film as the outermost layer may be formed by sequentially forming, by deposition, the at least one layer of another film and the deposited film on the incidence surface of the optical window. The at least one layer of another film may be formed to cover an entire surface of the incidence surface of the optical window, and a multilayer film of the at least one layer of another film and the deposited film may be formed on the entire surface of the incidence surface of the optical window.

An optical measurement device according to the present invention comprises the optical measurement probe and a detector for detecting light guided by the optical measurement probe.

Also, an optical measurement device according to the present invention comprises the optical measurement probe, wherein the optical measurement probe is attached to a cylinder head of an internal combustion engine in such a way as to look into a combustion chamber that is a measurement target.

According to the present invention, by covering the incidence surface of the optical window by the deposited film, adhesion of dirt to the incidence surface can be prevented, and a measurement result can be prevented from being affected by the adhesion of dirt to the incidence surface, and thus, a more stable measurement result can be obtained.

DETAILED DESCRIPTION OF THE PREFERRED EMBODIMENTS

Figure 1:
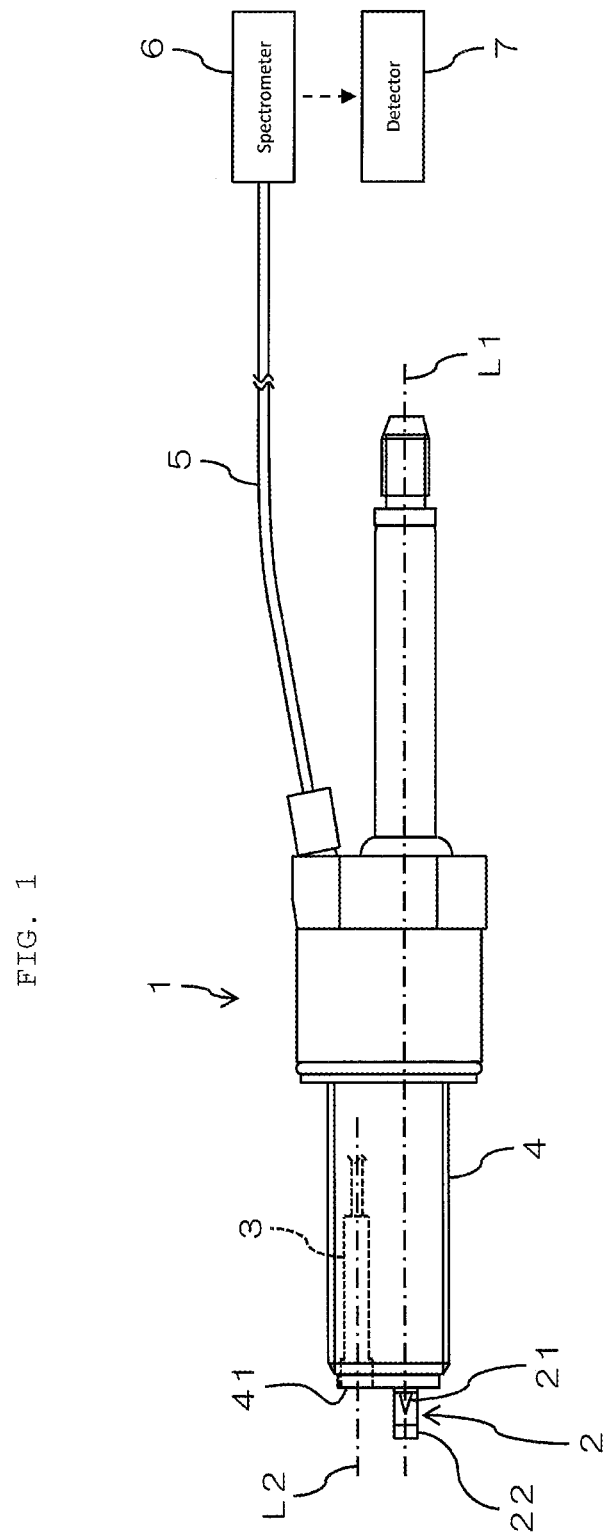
FIG. 1 is a view showing a structure example of an optical measurement device provided with an optical measurement probe according to an embodiment of the present invention.

FIG. 1 is a view showing a structure example of an optical measurement device provided with an optical measurement probe 1 according to an embodiment of the present invention. FIG. 1 shows a schematic side view of a concrete structure of the optical measurement probe 1, and also a block diagram of other structures.

The optical measurement probe 1 according to the present embodiment is for guiding light generated in a high temperature environment to an appliance, and is installed in a combustion chamber of an internal combustion engine of a car, a motorcycle or the like, and is used at a time of evaluating the combustion state in the combustion chamber, for example. The high temperature environment is an environment of 300° C. or higher, for example, and the optical measurement probe 1 according to the present embodiment is heat-resistant in an environment of 300° C. or higher, and more preferably, 800° C. or higher. Additionally, "heat resistance" here means a property according to which the optical property does not change even in the event of use in a high temperature environment as described above.

This optical measurement probe 1 is, for example, a plug built-in type optical measurement probe, and is structured by a spark section 2 and a light receiving section 3 being integrally held by a plug main body 4. Light received by the light receiving section 3 is guided to a spectrometer 6 via an optical fiber 5, which is an example of a light guide, and light dispersed by the spectrometer 6 is detected by a detector 7. Incidentally, the light guide is not restricted to the optical fiber 5 as long as it is structured to be able to guide light to an appliance.

The spark section 2 is provided with a center electrode 21 linearly protruding from an end face 41 of the plug main body 4, and a side electrode 22 protruding laterally to the center electrode 21 from the end face 41 of the plug main body 4 in an L-shaped manner. The center electrode 21 protrudes from the end face 41 along an axis L1 extending in a longitudinal direction of the plug main body 4.

With a general spark plug, the center electrode 21 extends along the center axis of the plug main body 4, but according to the optical measurement probe 1 of the present embodiment, to secure a space for holding the light receiving section 3 integrally with the spark section 2 by the plug main body 4, the center electrode 21 extends along the axis L1 that is shifted in parallel to the center axis of the plug main body 4.

The side electrode 22 protrudes from the end face 41 of the plug main body 4 in an L-shaped manner, and thus, its tip end portion faces the tip end of the center electrode 21 with a predetermined gap in the direction of the axis L1. The gap formed along the direction of the axis L1 between the tip end portion of the side electrode 22 and the center electrode 21 is a so-called electrode gap (a plug gap), and is formed to be about 0.5 to 2 mm, for example.

The side electrode 22 is a ground electrode for forming a ground, and applies a high voltage between the center electrode 21 and itself to thereby cause spark discharge between the electrodes and perform ignition. By this ignition by the spark section 2, fuel in the combustion chamber of the internal combustion engine is combusted and combustion gas is generated, and also, light generated at the time of combustion is received by the light receiving section 3.

Figure 2:
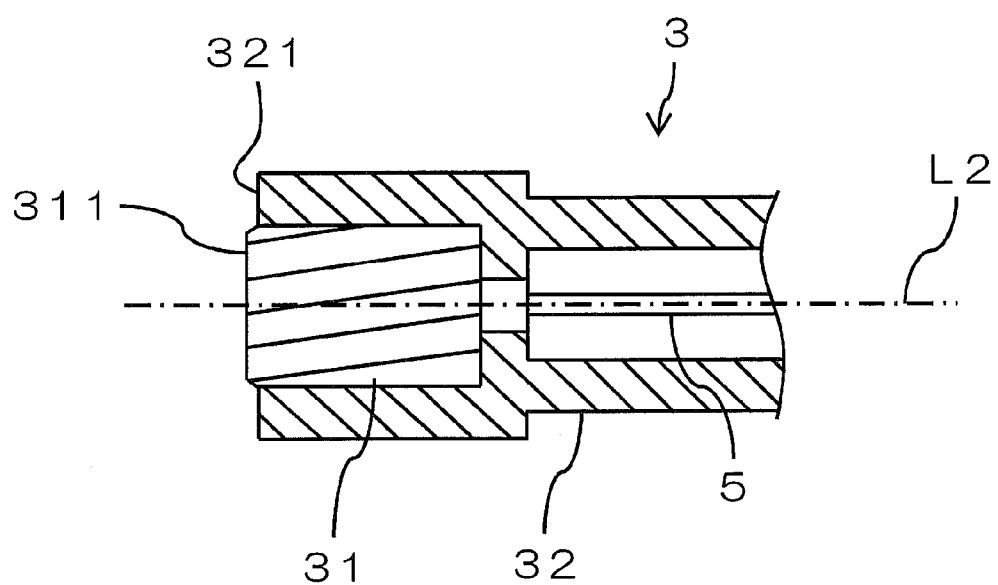
FIG. 2 is a cross-sectional view showing a structure example of a light receiving section.

FIG. 2 is a cross-sectional view showing a structure example of the light receiving section 3. The light receiving section 3 is provided with an optical window 31, a holder 32, and the like, and the tip end portion of the optical fiber 5 is attached to the holder 32. Additionally, in FIG. 2, only the surrounding structures of the optical window 31 of the light receiving section 3 are shown.

The optical window 31 is a transparent member formed of sapphire, for example, and is capable of transmitting, and introducing into the holder 32, light incident on the incidence surface 311. In this example, the optical window 31 is formed to be columnar, and light generated at the time of combustion is to enter from the end face of the optical window 31. The end face of the optical window 31 is formed into a circular shape, for example, and structures the incidence surface 311. However, the optical window 31 is not restricted to be columnar, and the incidence surface 311 is not restricted to be circular, and the optical window 31 may be formed by any other form.

The holder 32 is formed to be cylindrical, for example, and the optical window 31 is accommodated in one end portion of the holder 32. Specifically, a concave portion having an inner diameter corresponding to the outer diameter of the optical window 31 is formed at one end portion of the holder 32, and the optical window 31 is accommodated inside this concave portion. The gap between the inner circumferential surface of the concave portion and the outer circumferential surface of the optical window 31 is sealed by brazing, for example, and the combustion gas generated at the time of combustion is prevented from entering inside the holder 32.

In the case of brazing the optical window 31, the holder 32 is desirably formed of Kovar. However, the holder 32 may be formed of metals other than Kovar, such as stainless steel or aluminum, or may be formed of materials other than metal. Since an end portion of the optical fiber 5 is accommodated therein, the holder 32 is desirably formed of a material with high heat resistance.

The optical fiber 5 is provided inside the holder 32, extending along a center axis L2 of the holder 32, and the optical window 31 is arranged coaxially and with a slight gap to the optical fiber 5. Thereby, light transmitted through the optical window 31 enters the optical fiber 5 from the end portion, and is guided to an appliance such as the spectrometer 6 through the optical fiber 5. As shown in FIG. 1, the light receiving section 3 is held by the plug main body 4 in such a way that the center axis L2 extends in parallel to the axis L1 of the center electrode 21, and is provided in such a way that the incidence surface 311 of the optical window 31 is substantially flush with the end face 41 of the plug main body 4.

Additionally, in this example, the incidence surface 311 of the optical window 31 protrudes from an end face 321 of the holder 32 due to the optical window 31 being attached slightly raised from the end face 321 of the holder 32 along the center axis L2. However, this structure is not restrictive, and the incidence surface 311 of the optical window 31 may be provided to be flush with the end face 321 of the holder 32, for example.

Figure 3A:
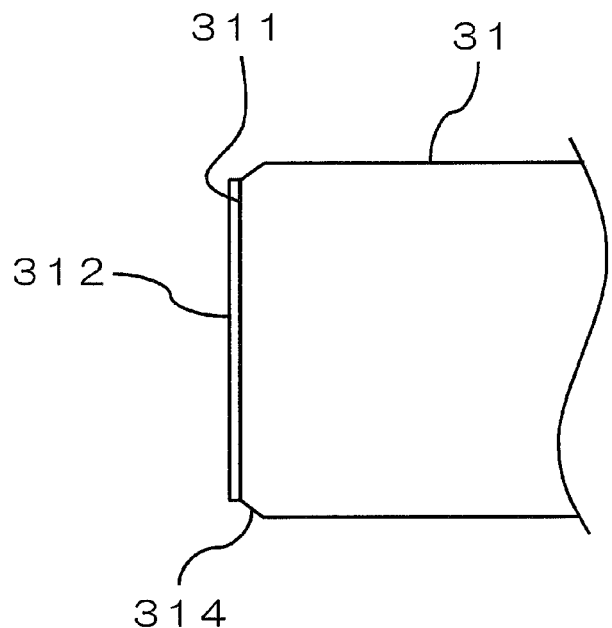
FIGS. 3A and 3B are side views showing structure examples of an optical window.
Figure 3B:
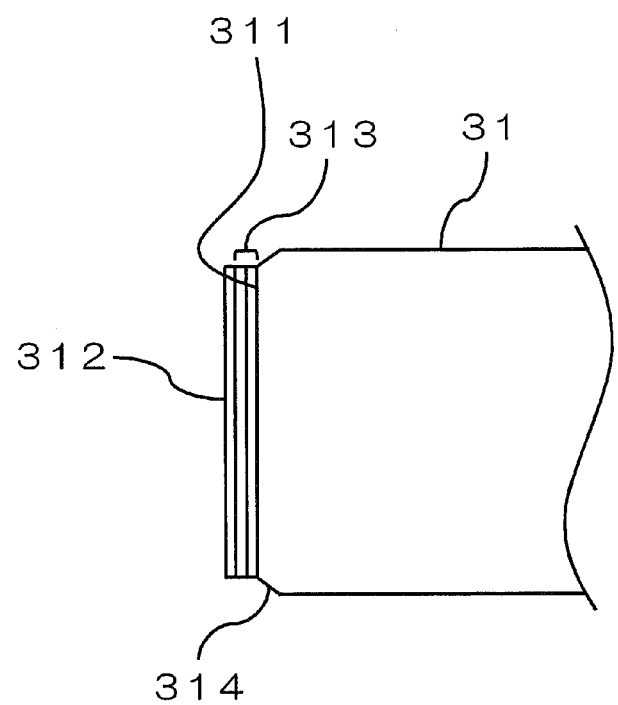

FIGS. 3A and 3B are side views showing structure examples of the optical window 31. As shown in FIGS. 3A and 3B, according to the present embodiment, the incidence surface 311 of the optical window 31 is covered by a deposited film 312. The deposited film 312 is formed from $SiO_2$, for example.

In the example in FIG. 3A, the deposited film 312 is formed directly on the incidence surface 311 of the optical window 31. On the other hand, in the example in FIG. 3B, a plurality of other films 313 are interposed between the deposited film 312 and the incidence surface 311 of the optical window 31, and a multilayer film having the deposited film 312 as the outermost layer is formed. The other films 313 in FIG. 3B can be sequentially formed on the incidence surface 311 by deposition, for example. Additionally, in FIGS. 3A and 3B, to facilitate understanding, the film thickness of each of the films 312 and 313 is shown to be greater than the actual thickness.

Each of the films 312 and 313 can be formed by various deposition methods such as ion plating, sputtering or vacuum deposition, for example. In this example, the deposited film 312 at the outermost layer is formed from $SiO_2$. The other films 313 in FIG. 3B do not have to include a plurality of layers, and it is enough if at least one other film 313 is interposed between the deposited film 312 and the incidence surface 311 of the optical window 31. Also, the other film(s) 313 may be formed to cover the entire surface of the incidence surface 311 of the optical window 31, and a multilayer film of the other film (s) 313 and the deposited film 312 may be formed on the entire surface of the incidence surface 311 of the optical window 31.

The other films 313 in FIG. 3B is formed of a material different from that of the deposited film 312 at the outermost layer to thereby provide an optical property specific to the material. As the optical property, for example, a property of preventing reflection of light, or a property of transmitting only the light of a specific wavelength can be cited, but these are not restrictive.

A tapered surface 314 is formed to the optical window 31 by chamfering of the outer circumferential edge of the end face on the side of the incidence surface 311, for example. Although, in the examples in FIGS. 3A and 3B, the films 312 and 313 are not formed on the part of the tapered surface 314 of the optical window 31, the films 312 and 313 may also be formed on the part of the tapered surface 314.

According to the present embodiment, adhesion of dirt to the incidence surface 311 of the optical window 31 used in a high temperature environment can be prevented by covering the incidence surface 311 by the deposited film 312. That is, in a case where the optical window 31 is formed of a material with high heat resistance, such as sapphire, dirt may easily adhere to the incidence surface 311 depending on the material, but even in such a case, adhesion of dirt to the incidence surface 311 can be prevented by covering the incidence surface 311 by the deposited film 312. A measurement result can thereby be prevented from being affected by the adhesion of dirt to the incidence surface 311, and a more stable measurement result can be obtained.

Particularly, according to the present embodiment, by covering the incidence surface 311 of the optical window 31 formed of sapphire by the deposited film 312, adhesion of dirt to the incidence surface 311 can be prevented. The optical window 31 formed of sapphire is highly heat-resistant and is capable of transmitting light of a wide wavelength range, and is thus suitable for use in a high temperature environment, but on the other hand, it is highly lipophilic, and greasy dirt easily adheres thereto. Accordingly, as in the present embodiment, with respect to the optical measurement probe 1 to be used in an environment where the temperature is high and adhesion of greasy dirt easily occurs, adhesion of greasy dirt to the incidence surface 311 of the optical window 31 formed of sapphire can be prevented by covering the incidence surface 311 by the deposited film 312. Thus, a more stable measurement result can be obtained even in an environment where the temperature is high and adhesion of greasy dirt easily occurs.

The optical window 31 is not limited to be of sapphire, and an alternative material that satisfies the conditions of high heat resistance and transmission of light of a wide wavelength range can also be used.

Moreover, according to the present embodiment, by covering the incidence surface 311 of the optical window 31 by the deposited film 312 formed from $SiO_2$, adhesion of dirt to the incidence surface 311 can be prevented. The deposited film 312 formed from $SiO_2$ is capable of transmitting light of a wide wavelength range, and dirt is not easily adhered thereto. Thus, with respect to the optical measurement probe 1 that is used in an environment where adhesion of greasy dirt easily occurs, as in the present embodiment, by covering the incidence surface 311 of the optical window 31 by the deposited film 312 formed from $SiO_2$, adhesion of greasy dirt to the incidence surface 311 can be prevented, and also, the deposited film 312 can be prevented from causing reduction in the optical property. Accordingly, a more stable measurement result can be obtained even in an environment where adhesion of greasy dirt easily occurs.

Particularly, according to a structure where the incidence surface 311 of the optical window 31 formed of sapphire is covered by the deposited film 312 formed from $SiO_2$, as in the present embodiment, the optical measurement probe 1 which is very suitable for use in an environment where the temperature is high and adhesion of greasy dirt easily occurs, like the inside of the combustion chamber of an internal combustion engine, can be provided.

Incidentally, the deposited film 312 covering the incidence surface 311 of the optical window 31 may be formed from other materials such as $TiO_2$ without being restricted to $SiO_2$. In this case, in order to use the optical window 31 in an environment where adhesion of dirt easily occurs, the material for the deposited film 312 is desirably such that dirt does not easily adhere thereto and light of a wide wavelength range can be transmitted. For example, the deposited film 312 may be formed of a material having an opposite property to the optical window 31 with respect to at least one of lipophilicity, hydrophilicity, and thermal conductivity.

In the example in FIG. 3A, adhesion of dirt to the incidence surface 311 of the optical window 31 can be prevented by a simple structure of forming the deposited film 312 directly on the incidence surface 311. Accordingly, a measurement result can be effectively prevented from being affected by adhesion of dirt to the incidence surface 311 by an inexpensive structure, and a more stable measurement result can be obtained.

On the other hand, in the example in FIG. 3B, by interposing the other films 313 between the deposited film 312 and the incidence surface 311, an optical property specific to the films 313 can be provided. Thereby, adhesion of dirt to the incidence surface 311 can be prevented, and the optical measurement probe 1 provided with an optical property suitable for the use environment can be provided.

Figure 4:
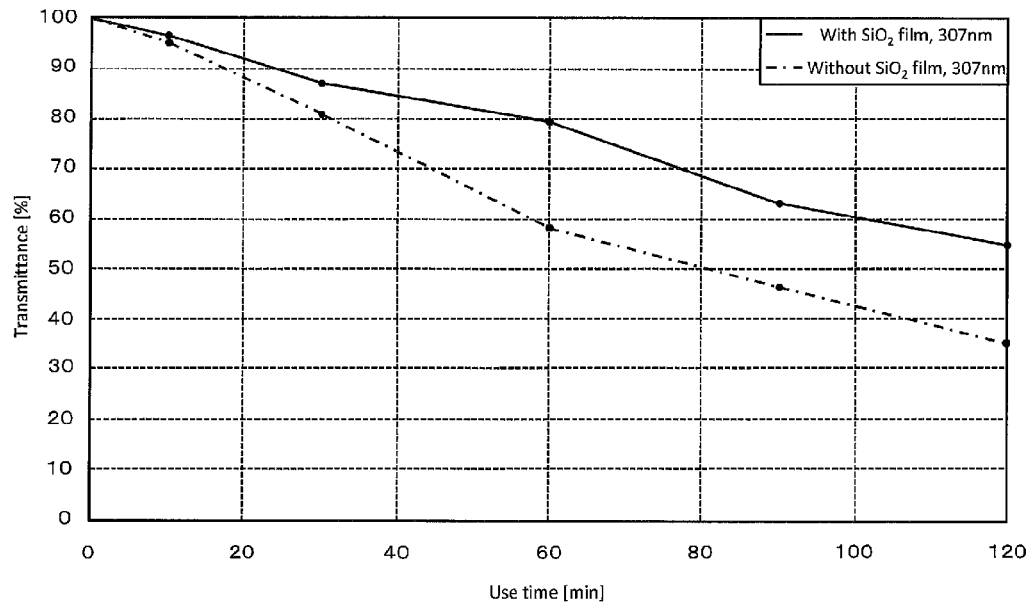
FIG. 4 is a graph showing the difference in the transmittance of the optical window due to presence or absence of a deposited film, based on the relationship to the use time, showing measurement results regarding light emission of OH radical that enters an incidence surface of the optical window.
Figure 5:
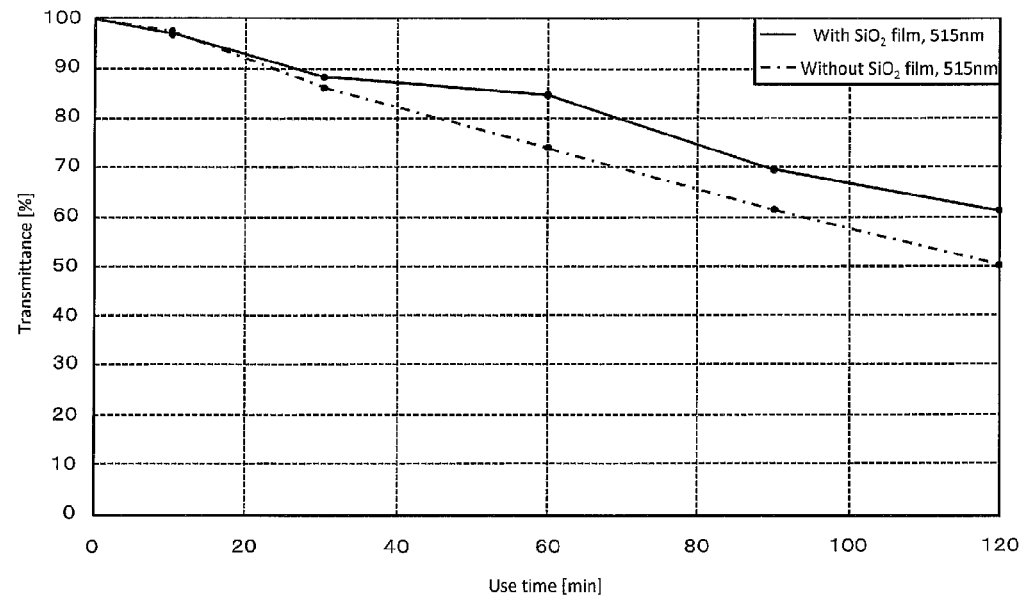
FIG. 5 is a graph showing the difference in the transmittance of the optical window due to presence or absence of the deposited film, based on the relationship to the use time, showing measurement results regarding light emission of $C_2$ radical that enters the incidence surface of the optical window.

FIGS. 4 and 5 are graphs showing the difference in the transmittance of the optical window 31 due to presence or absence of the deposited film 312, based on the relationship to the use time. FIG. 4 shows measurement results regarding light emission of OH radical (307.5 nm) that enters the incidence surface 311 of the optical window 31. On the other hand, FIG. 5 shows measurement results regarding light emission of $C_2$ radical (515.5 nm) that enters the incidence surface 311 of the optical window 31. These measurement results are results of measuring a change in the transmittance of the optical window 31 under the same condition and at regular intervals while arranging the optical measurement probe 1 to look into the combustion chamber of the same internal combustion engine.

As shown by the solid lines in FIGS. 4 and 5, in the case of a structure where the incidence surface 311 of the optical window 31 is covered by the deposited film 312 of $SiO_2$, the degree of reduction in the transmittance caused by lapse of use time is lower compared to the cases, shown by the dashed lines, where the deposited film 312 of $SiO_2$ is not provided. It can be seen from the results that, by covering the incidence surface 311 of the optical window 31 by the deposited film 312 of $SiO_2$, dirt is less likely to adhere to the incidence surface 311, and the influence of the dirt on the measurement result can be reduced.

Figure 6:
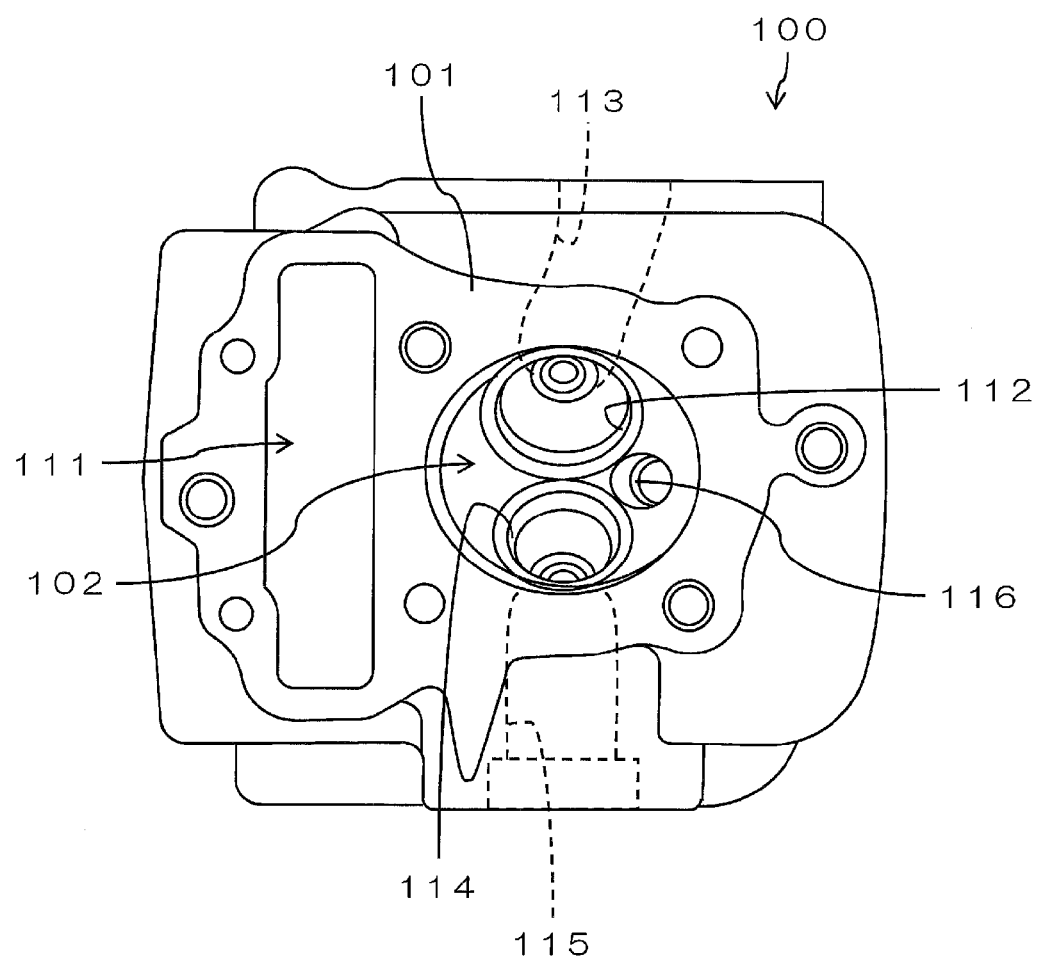
FIG. 6 is a view for describing the attachment position of the optical measurement probe in a cylinder head.

FIG. 6 is a view for describing the attachment position of the optical measurement probe 1 in a cylinder head 101. For example, the cylinder head 101, and a combustion chamber 102 surrounded by a cylinder block and a piston that are not shown are formed in the internal combustion engine 100 of a car or a motorcycle, for example.

The optical measurement probe 1 is attached to the cylinder head 101 in such a way as to look into the combustion chamber 102, which is a measurement target, for example. Specifically, a valve system interlocking member accommodation chamber 111 for accommodating a valve system interlocking member (for example, a cam chain or the like), not shown, is formed on the cylinder head 101, and the optical measurement probe 1 is arranged in such a way as to look into the combustion chamber 102 from an opening 116 formed on the opposite side of the valve system interlocking member accommodation chamber 111 across the cylinder center.

An intake port 113 that is communicated with an intake valve opening 112 opened to the combustion chamber 102, and an exhaust port 115 that is communicated with an exhaust valve opening 114 opened to the combustion chamber 102 are formed on the cylinder head 101. In this example, the opening 116 that is open to the combustion chamber 102 is formed near the intake valve opening 112 and the exhaust valve opening 114 of the cylinder head 101, and the optical measurement probe 1 is attached inside the opening 116. Accordingly, for example, at the time of evaluating the combustion state in the combustion chamber 102 of the internal combustion engine 100, light generated in the combustion chamber 102 can be guided to an appliance through the optical measurement probe 1 attached inside the opening 116.

Additionally, the optical measurement probe 1 according to the present invention is not limited to be installed in the combustion chamber 102 of the internal combustion engine 100 of a car, a motorcycle or the like, and can be installed in any high temperature environment to guide light generated at the time of combustion to an appliance.

Also, the present invention is not limited to a plug built-in type optical measurement probe where the spark section 2 and the light receiving section 3 are integrally held by the plug main body 4, and can also be applied to a structure where the light receiving section 3 is attached to another member, or to an optical measurement probe including only the light receiving section 3, for example. In this case, the optical measurement probe may be attached to another opening (not shown) that is open to the combustion chamber 102.

What is claimed is:

1. An optical measurement probe structured to guide light generated in a high temperature environment to an appliance, comprising:
   an optical window for transmitting light incident on an incidence surface; and
   a light guide for guiding light which has passed through the optical window to the appliance,
   wherein the incident surface of the optical window is covered by a deposited protective film which is formed from a lipophobic material and which protects the window from greasy dirt.

2. The optical measurement probe according to claim 1, wherein the optical window is formed of sapphire.

3. The optical measurement probe according to claim 1, wherein the deposited film is formed from $SiO_2$.

4. The optical measurement probe according to claim 1, wherein the deposited film is formed directly on the incidence surface.

5. The optical measurement probe according to claim 1, wherein at least one layer of another film is interposed between the deposited film and the incidence surface.

6. The optical measurement probe according to claim 5, wherein the at least one layer of another film is formed to cover an entire surface of the incidence surface of the optical window, and wherein a multilayer film of the at least one layer of another film and the deposited film is formed on the entire surface of the incidence surface of the optical window.

7. An optical measurement device comprising:
the optical measurement probe according to claim 1; and
a detector for detecting light guided by the optical measurement probe.

8. An optical measurement device, wherein the optical measurement probe according to claim 1 is attached to a cylinder head of an internal combustion engine in such a way as to look into a combustion chamber that is a measurement target.

9. The optical measurement probe of claim 1, wherein the probe is heat-resistant in an environment of 300° C. or higher.

10. The optical measurement probe of claim 1, wherein the probe is heat-resistant in an environment of 800° C. or higher.

11. The optical measurement probe of claim 1, wherein the deposited film is formed from $TiO_2$.

12. The optical measurement probe of claim 1, wherein the light guide is an optical fiber.

13. The optical measurement probe of claim 1, further comprising a holder for accommodating the optical window at an end portion,
wherein the incident surface of the optical window is directed outward of the holder.

* * * * *